United States Patent
Poindexter et al.

(10) Patent No.: US 6,596,724 B2
(45) Date of Patent: Jul. 22, 2003

(54) OXADIAZOLE AND THIADIAZOLE DERIVATIVES OF DIHYDROPYRIDINE NPY ANTAGONISTS

(75) Inventors: Graham S. Poindexter, Old Saybrook, CT (US); Mendi Higgins, Middletown, CT (US); James Guy Breitenbucher, Escondido, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/897,532

(22) Filed: Jul. 2, 2001

(65) Prior Publication Data

US 2002/0013323 A1 Jan. 31, 2002

Related U.S. Application Data

(60) Provisional application No. 60/216,985, filed on Jul. 7, 2000.

(51) Int. Cl.$^7$ ............... A61K 31/495; A61K 31/50; A61K 31/445; C07D 401/00; C07D 417/00
(52) U.S. Cl. ............... 514/253.1; 514/253.13; 514/316; 514/318; 514/342; 544/364; 544/365; 546/187; 546/194; 546/268.7
(58) Field of Search ............... 546/194, 187, 546/268.7; 514/318, 253.1, 253.13, 316, 342; 544/365, 364

(56) References Cited

U.S. PATENT DOCUMENTS

| | | | |
|---|---|---|---|
| 4,829,076 A | 5/1989 | Szilágyi et al. | 514/356 |
| 5,554,621 A | 9/1996 | Poindexter et al. | 514/278 |
| 5,635,503 A | 6/1997 | Poindexter et al. | 514/218 |
| 5,668,151 A | 9/1997 | Poindexter et al. | 514/318 |

OTHER PUBLICATIONS

Chauraisia, et al., "Nonpeptidomimetic antagonists of the Neuropeptide Y Receptor: Benextramine Analogs with Selectivity for the Peripheral $Y_2$ Receptor," *J. Med. Chem.*, 1994, 37, 2242–48.

Rudolf, et al., "The first highly potent and selective non–peptide neuropeptide Y $Y_1$ receptor antagonist: BIBP3226," *Eur. J. Pharmacol.*, 1994, 271, R11–R13.

Serradeil–LeGal, et al., SR120819A, an orally–active and selective neuropeptide Y $Y_1$ receptor antagonist, *FEBS Lett.*, 1995, 362, 192–96.

*Primary Examiner*—Brenda Coleman
(74) *Attorney, Agent, or Firm*—Richard P. Ryan

(57) ABSTRACT

A series of non-peptidergic antagonists of NPY have been synthesized and are comprised of oxadiazole, thiadiazole and thiadiazole oxide derivatives of dihydropyridines of Formula I.

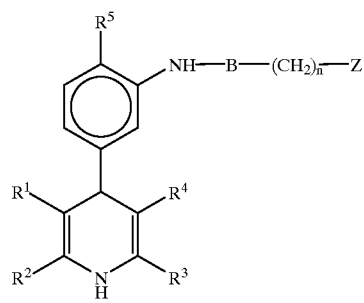

wherein B is

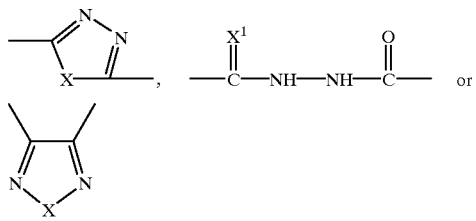

with X being O, S or

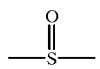

and $X^1$ is O or S. As antagonists of NPY-induced behavior, these compounds are expected to act as effective anorexiant agents in promoting weight loss and treating eating disorders.

17 Claims, No Drawings

OXADIAZOLE AND THIADIAZOLE DERIVATIVES OF DIHYDROPYRIDINE NPY ANTAGONISTS

CROSS REFERENCE TO RELATED APPLICATION

This non-provisional application claims priority from provisional application U.S. Ser. No. 60/216,985 filed Jul. 7, 2000.

FIELD OF THE INVENTION

The present invention is directed to heterocyclic compounds comprising dihydropyridines having oxadiazole, thiadiazole, acylsemicarbazide and thioacylsemicarbazide moieties connected to the 4-position of the pyridine ring. More particularly, the invention is directed to NPY antagonist of oxadiazole and thiadiazole derivatives of 1,4-dihydropyridine.

BACKGROUND OF THE INVENTION

Neuropeptide Y (NPY) is a 36 amino acid peptide first isolated in 1982 from porcine brain. The peptide is a member of a larger peptide family which also includes peptide YY (PYY), pancreatic peptide (PP), and the non-mammalian fish pancreatic peptide Y (PY). Neuropeptide Y is very highly conserved in a variety of animal, reptile and fish species. It is found in many central and peripheral sympathetic neutrons and is the most abundant peptide observed in the mammalian brain. In the brain, NPY is found most abundantly in limbic regions. The peptide has been found to elicit a number of physiological responses including appetite stimulation, anxiolysis, hypertension, and the regulation of coronary tone.

Structure-activity studies with a variety of peptide analogs (fragments, alanine replacements, point mutations, and internal deletion/cyclized derivatives) suggest a number of receptor subtypes exist for NPY. These currently include the $Y_1$, $Y_2$, $Y_3$, and the $Y_{1-like}$ or $Y_4$ subtypes.

Although a number of specific peptidic antagonists have been identified for most of the subtypes, few selective non-peptidic antagonists have been reported to date. The heterocyclic guanidine derivative He 90481 (4) was found to be a weak but competitive antagonist of NPY-induced $Ca^{++}$ entry in HEL cells ($pA_2$=4.43). The compound was also found to have $\alpha_2$-adrenergic and histaminergic activity at this dose range. D-Myo-inositol-1,2,6-triphosphate was reported to be a potent but non-competitive antagonist to NPY-induced contractions in guinea pig basilar artery. Similarly, the benextramine-like bisguanidines were reported to displace $^3$H-NPY in rat brain ($IC_{50}$, 19 and 18.4 $\mu$M) and to display functional antagonism in rat femoral artery. The bisguanidine was shown to be functionally selective for the $Y_2$ receptor since it antagonized the effect of the $NPY_2$ agonist $NPY_{13-36}$ but had no effect on the vasoconstrictive activity of the $NPY_1$ agonist [$Leu^{31}$, $Pro^{34}$] NPY as disclosed in *J. Med. Chem.*, 1994, 37, 2242–48, C. Chauraisia, et al.

Compound BIBP 3226, as reported in K. Rudolf, et al., *Eur. J. Pharmacol.*, 1994, 271, R11–R13, displaces I-125 Bolton-Hunter labeled NPY in human neuroblastoma cells (SK-N-MC). BIBP antagonized the NPY-induced increase in intracellular $Ca^{++}$ in SK-N-MC cells as well as antagonizing the NPY-induced pressor response in pithed rat experiments.

In addition to displacing I-125 labeled NPY and PYY in human neuroblastoma cells, compound SR 120819A, as reported in C. Serradeil-LeGal, et al., *FEBS Lett.*, 1995, 362, 192–A6, also antagonized NPY-related increases in diastolic blood pressure in an anesthetized guinea pig model.

Over the past two decades, extensive work has been conducted relating to the 4-aryl-1,4-dihydropyridine class of compounds. Syntheses of compounds in this category have been driven by their pharmacological actions involving calcium channels rendering them useful for treating cardiovascular disorders such as ischemia and hypertension.

Numerous prior patents and publications disclose various dihydropyridine derivatives. One example is U.S. Pat. No. 4,829,076 to Szilagyi, et al. disclosing compounds of formula (1) as calcium antagonists for treating hypertension.

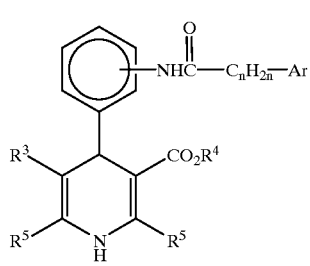

(1)

U.S. Pat. No. 5,635,503 to Poindexter, et al. discloses 4-(3-substituted-phenyl)-1,4-dihydropyridine derivatives having NPY antagonist properties. These derivatives conform to structural formula (2).

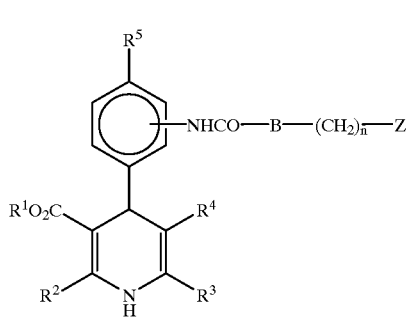

(2)

In (2), B is either a covalent bond or the group —NH—. The symbol Z denotes hetaryl moieties, examples being homopiperazinyl or piperazine.

U.S. Pat. No. 5,554,621 discloses related derivatives where Z is a fused ring or a spiro-fused nitrogen heterocycle. U.S. Pat. No. 5,668,151 also discloses related derivatives where Z is a piperidinyl or tetrahydropyrindinyl.

The above-noted compounds have shown to posses antagonist activity. However, there is a continuing need for dihydropyridine derivatives having improved NPY antagonist activity.

SUMMARY OF THE INVENTION

The present invention is directed to novel dihydropyridine derivatives having NPY antagonist activity. More particularly, the invention is directed to oxadiazole and thiadiazole derivatives of dihydropyridines.

Accordingly, one aspect of the invention is to provide dihydropyridine derivatives that are effective in promoting weight loss and treating certain disorders in a mammal by administering to the mammal an anorexiant effective dose of an active compound of the invention.

A further aspect of the invention is to provide a method of treating clinical disorders amenable to alleviation by eliciting an NPY $Y_1$ response by administering to a patient an effective amount of a compound of the invention.

Another aspect of the invention is to provide a pharmaceutical composition for use in promoting weight loss and treating eating disorders, where the composition comprises an anorexiant effective amount of an active compound of the invention and a pharmaceutically acceptable carrier.

The compounds of the invention have the Formula I and its pharmaceutically acceptable acid addition salts or hydrates thereof

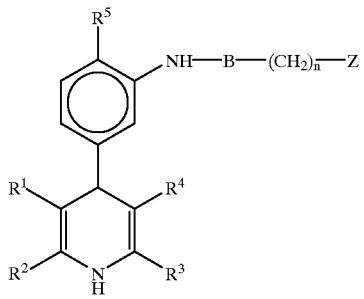

(I)

wherein B is

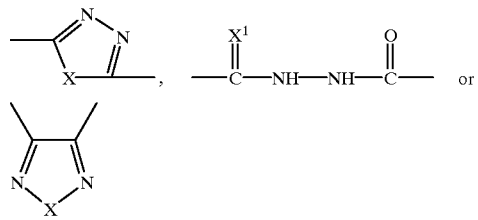

with X being O, S or

and $X^1$ is O or S;

$R^1$ and $R^4$ are independently selected from $CO_2R^6$, cyano, and

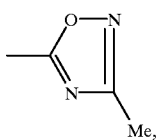

where $R^6$ is a lower alkyl;

$R^2$ and $R^3$ are independently selected from hydrogen, cyano and lower alkyl;

$R^5$ is selected from hydrogen and halogen;

n is an integer selected from 1 to 5;

Z is 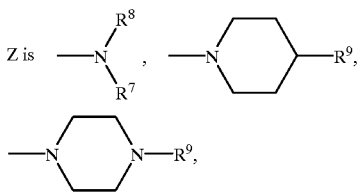

in which $R^7$ and $R^8$ are independently selected from lower alkyl and lower alkanol; $R^9$ is selected from hydrogen, lower alkyl, $-CO_2R^6$, $-(CH_2)_mR^{10}$, hydroxy, cyano, and $-(CH_2)_mNR^{11}R^{12}$, wherein m is zero or an integer from 1 to 3;

$R^{10}$ is $C_{3-7}$ cycloalkyl, naphthyl, and

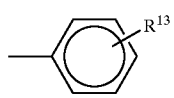

with $R^{13}$ selected from the group consisting of lower alkyl, lower alkenyl, $C_{3-7}$ cycloalkyl, lower alkoxy, hydrogen, halogen, hydroxy, dialkylamino, phenoxy, amino, $-NHCOR^6$, $-CO_2R^6$, $NO_2$, trifluoromethyl, and phenyl, and $R^{11}$ and $R^{12}$ are independently selected from the group consisting of hydrogen, alkyl, cycloalkyl, alkylene, phenyl, alkylamino, heterocyclic alkyl, methoxy, cyano, lower alkanol, naphthyl, furfuryl, tetrahydrofurfuryl, thiophene, azetidine, lower alkyl esters, acetamides, and carbamates and where $-NR^{11}R^{12}$ is a heterocyclic amine or imine.

These and other aspects of the invention will become apparent to one skilled in the art as described in the following detailed description.

DETAILED DESCRIPTION OF THE INVENTION

The present invention is directed to novel compounds having NPY $Y_1$ antagonist activity and pharmaceutical compositions containing the novel compounds. The invention is further directed to a method of treating clinical disorders, such as eating disorders, using the novel compounds of the invention.

The compounds of the invention have the Formula I

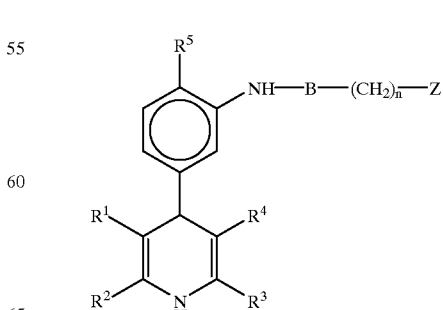

(I)

The compounds within the perview of the invention include the pharmaceutically acceptable acid addition salts and/or hydrates of the compounds of Formula I.

In the Formula I, B is

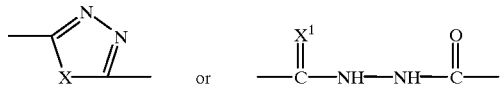

where X is O, S or

and $X^1$ is O or S;
wherein
  $R^1$ and $R^4$ are independently selected from $CO_2R^6$, cyano, and

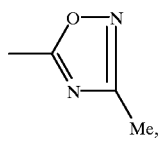

where $R^6$ is a lower alkyl;
  $R^2$ and $R^3$ are independently selected from hydrogen, cyano and lower alkyl;
  $R^5$ is selected from hydrogen and halogen;
  n is an integer selected from 1 to 5;
  Z is

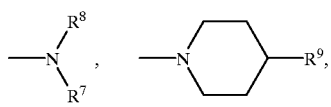

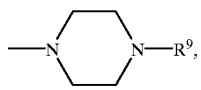

in which $R^7$ and $R^8$ are independently selected from lower alkyl and lower alkanol; $R^9$ is selected from hydrogen, lower alkyl, $-CO_2R^6$, $-(CH_2)_mR^{10}$, hydroxy, cyano, and $-(CH_2)_mNR^{11}R^{12}$, wherein
  m is zero or an integer from 1 to 3;
  $R^{10}$ is $C_{3-7}$ cycloalkyl, naphthyl, and

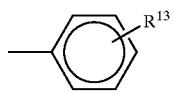

with $R^{13}$ being lower alkyl, lower alkenyl, $C_{3-7}$ cycloalkyl, lower alkoxy, hydrogen, halogen, hydroxy, dialkylamino, phenoxy, amino, $-NHCOR^1$, $-CO_2R^1$, $NO_2$, trifluoromethyl, phenyl, and $R^{11}$ and $R^{12}$ are independently selected from the group consisting of hydrogen, alkyl, cycloalkyl, alkylene, phenyl, alkylamino, heterocyclic alkyl, methoxy, cyano, lower alkanol, naphthyl, furfuryl, tetrahydrofurfuryl, thiophene, azetidine, lower alkyl esters, acetamides, and carbamates and where $-NR^{11}R^{12}$ is a heterocyclic amine or imine.

The term "lower" refers to substituents such as alkyl or alkoxy groups that contain from one to four carbon atoms. Alkenyl groups generally contain two to four carbon atoms. In embodiments of the invention, $R^1$ is preferably $CO_2R^6$ where $R^6$ is methyl. $R^2$ and $R^3$ are preferably methyl. $R^5$ is preferably hydrogen or fluorine. Z is preferably 4-(3-methoxyphenyl)-1-piperidinyl, 4-(cyclohexyl)-1-piperazinyl or 4-phenyl-1-piperazinyl.

The compounds of the present invention can exist as optical isomers and both the racemic mixtures of these isomers as well as the individual optical isomers themselves are within the scope of the present invention. The racemic mixtures can be separated into their individual isomers through well-known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, dichloroacetic acid, tartaric acid, lactic acid, succinic acid, citric acid, maleic acid, fumaric acid, sorbic acid, aconitic acid, salicyclic acid, phthalic acid, enanthic acid, and the like.

The dihydropyridine oxadiazole compounds of Formula I can be prepared by several processes. Generally, an amine (II), such as a piperidine or piperazine is alkylated with either methyl bromoacetate, methyl acrylate or ethyl 3-bromobutanoate to yield the corresponding ester (III). The ester (III) is then converted to the hydrazide derivative (IV) by treating with hydrazine in refluxing ethanol. The hydrazide (IV) is reacted with the starting dihydropyridine isocyanate (V) to form the acyl- or thioacylsemicarbazides (VI). The process proceeds according to the following Scheme.

SCHEME 1

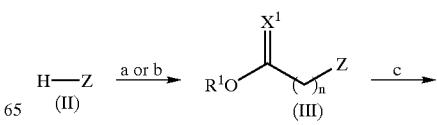

7

-continued

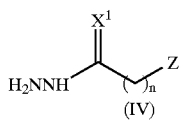
(IV)

a: Br—(CH$_2$)$_n$CO$_2$R, K$_2$CO$_3$, MeCN (n = 1 or 3)
b: Methyl acrylate (neat)
c: NH$_2$NH$_2$, EtOH

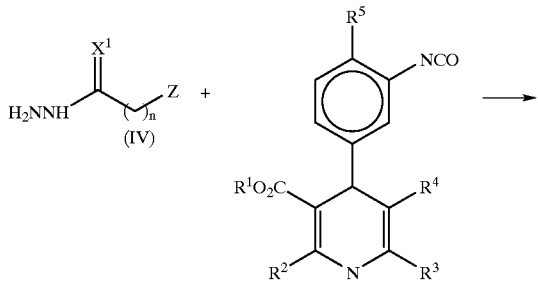

8

-continued

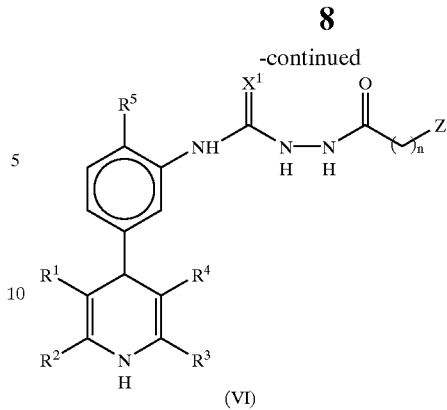
(VI)

The isocyanate (V) can be produced by various processes as known in the art. For example, the starting aniline dihydropyridine (VII) can be converted to the carbamate (VIII) with ClCO$_2$Me with pyridine in dichloromethane. The carbamate (VIII) is then converted to the isocyanate (V) by reacting with B-catecholborane with Et$_3$N in THF using the method of V. L. K. Valli and H. Alper, *J. Org. Chem.*, 1995, 60, 257–258. The isocyanate can be produced according to the following Scheme.

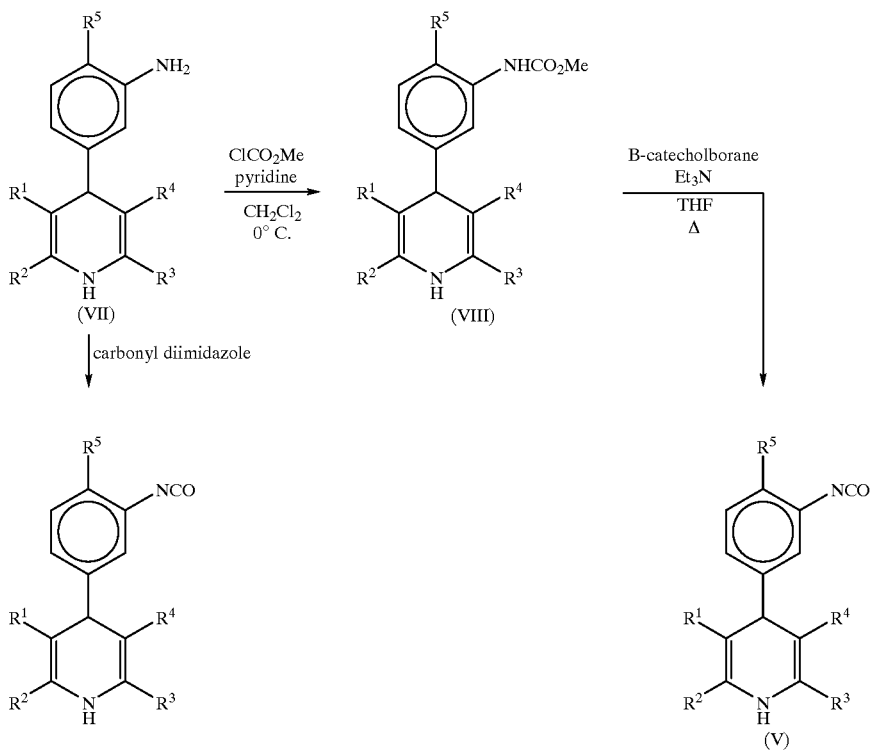

A preferred method for producing the oxadiazoles or thiadiazoles of Formula (I) forms a solution of the acyl- or thioacylsemicarbazide (VI) in 1,2-dichloroethane. PPh₃ and CCl₄ are then added to the solution and stirred. The solvent is removed and purified by flash chromatography.

The oxadiazoles and thiadiazoles also can be prepared by an alternative method by treating the acyl- or thioacylsemicarbazide with POCl₃ in toluene by heating with a steam bath. The oxadiazole and thiadiazole of Formula Ia are produced from the isocyanate derivative according to the following Scheme.

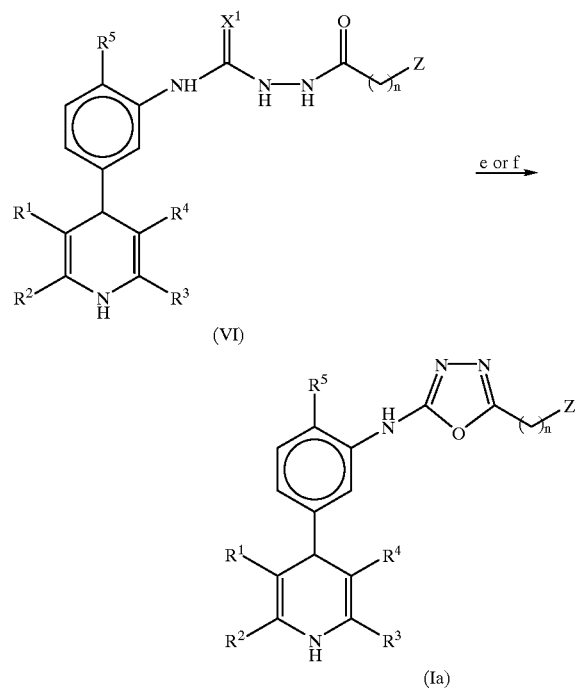

e: POCl₃, steam bath
f: PPh₃/CCl₄, 1,2-dichloroethane, reflux

In an alternative process of producing the thiadiazole of Formula Ib, the corresponding acylsemicarbazide (VIa) is treated with Lawesson's reagent in toluene and warmed to reflux. The process proceeds according to the following Scheme.

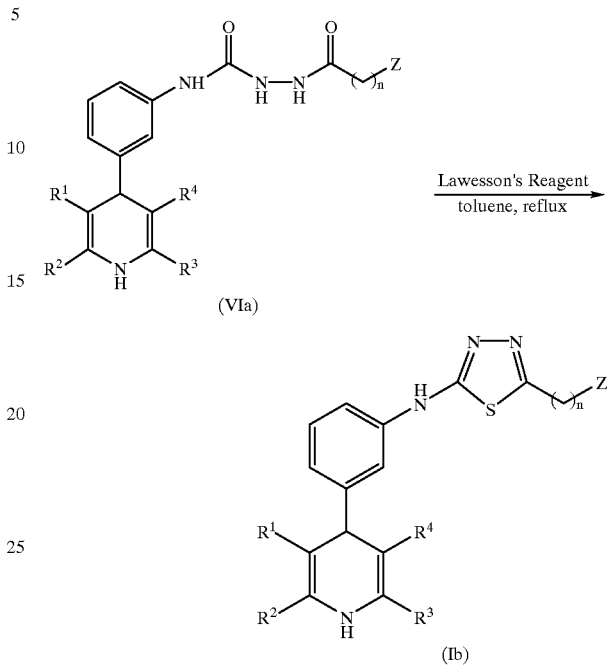

The synthesis of the thiadiazole oxide was accomplished according to the Scheme below. The aniline dihydropyridine (V) is converted to the thiadiazole oxide (IX) intermediate by way of AlMe₃ and Weinstock's alkylating agent (S. Karady, J. S. Amato, D. Dortmond, L. M. Weinstock, *Heterocycles*, 1981, 16, 1561–1568). The thiadiazole oxide intermediate (IX) is converted to the thiadiazole oxide of Formula I by alkylation with an amine. By way of example, the thiadiazole oxide intermediate (IX) is converted to the thiadiazole oxide of Formula (XI) by alkylation with 4-(3-methoxyphenyl)-1-piperdinepropanamine (XII).

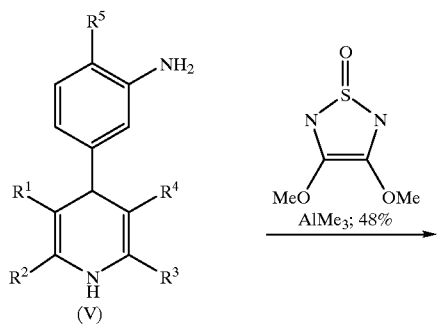

-continued

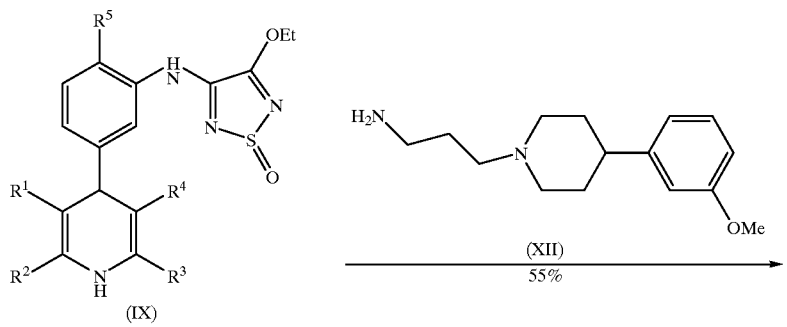

(IX) (XII) 55%

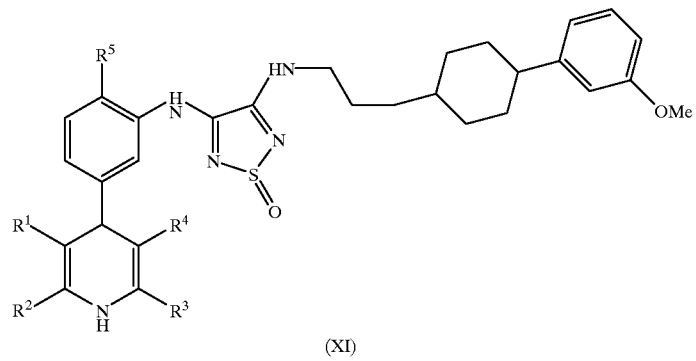

(XI)

The alkyl amines, such as the propanamines are produced by known processes. The amines can be produced from the appropriate secondary amines by conjugate addition to acrylonitrile in methanol. The reaction product is then hydrogenated catalytically in the presence of a Raney nickel catalyst in methanol to yield the amine as follows.

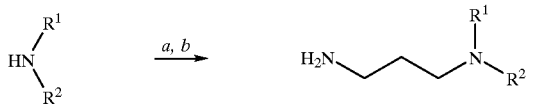

a: acrylonitrile, MeOH, Δ. b: $H_2$, $NH_3$, Raney Nickel, MeOH.

The alkyl piperazine can be synthesized using standard procedures by N-alkylation of the respective piperazine followed by removal of the Boc protecting groups as follows.

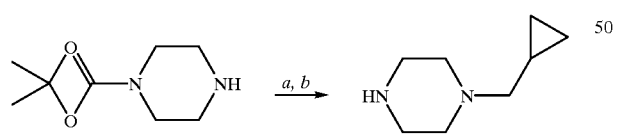

a: (Bromomethyl)cyclopropane, $K_2CO_3$, MeCN, Δ. b: 3N HCl, MeOH.

The Boc protecting group can also be cleaved from the intermediate in methanol and HCl to produce the unsubstituted piperazine derivative as follows.

The compounds of the invention demonstrate binding affinity at NPY $Y_1$ receptors. This pharmacologic activity is assayed in SK-N-MC (human neuroblastoma) cell membranes using iodine-125-labeled I-PYY as a radioligand. The compounds of Formula I had good binding affinities as evidenced by $IC_{50}$ values being about 10 μM or less at NPY $Y_1$ receptors. Preferred compounds have $IC_{50}$ values less than 100 nM and most preferred compounds have $IC_{50}$ values of less than 10 nM.

Pharmacologically, the compounds of Formula I act as selective NPY antagonists at NPY $Y_1$ receptor sites. As such, the compounds of Formula I are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:
  disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrhythmia, peripheral vascular disease, and abnormal renal conditions such as impaired flow of fluid, abnormal mass transport, or renal failure;
  conditions related to increased sympathetic nerve activity for example, during or after coronary artery surgery, and operations and surgery in the gastrointestinal track;
  cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;
  conditions related to pain or nociception;
  diseases related to abnormal gastrointestinal motility and secretion, such as different forms of ileus, urinary incontinence, and Crohn's disease;

abnormal drink and food intake disorders, such as obesity, anorexia, bulemia, and metabolic disorders;

diseases related to sexual dysfunction and reproductive disorders such as benign prostatic hyperplasia and male erectile dysfunction;

conditions or disorders associated with inflammation;

respiratory diseases, such as asthma and conditions related to asthma and bronchoconstriction;

diseases related to abnormal hormone release, such as leutinizing hormone, growth hormone, insulin and prolactin; and sleep disturbance and diabetes.

There is evidence that NPY contributes to certain symptoms in these disorders, such as, hypertension, eating disorders, and depression/anxiety, as well as circadian rhythms. Compounds of this invention are expected to be useful in treating these disorders as well as sleep disturbance and diabetes.

Selected compounds are tested further for their ability to block or stimulate NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a Formula I compound or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 50 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat the various diseases, conditions, and disorders listed above.

Therapeutically, the compounds of Formula I are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier. The carrier comprises one or more solid, semi-solid, or liquid diluent, filler, and formulation adjuvant that is non-toxic, inert and pharmaceutically acceptable.

Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the predetermined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate).

Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerin, propylene glycol, and polyethylene glycols or mixtures thereof. The polyethylene glycols consist of a mixture of non-volatile, usually liquid, polyethylene glycols which are soluble in both water and organic liquids and which have molecular weights from about 200 to 1500.

DESCRIPTION OF THE SPECIFIC EMBODIMENTS

The compounds of Formula I were prepared in the following Examples. All catalytic hydrogenations were performed with Parr Hydrogenators (Parr Instrument Co.) Bulb-to-bulb distillations were carried out on a Kugelrohr apparatus (Aldrich). Solvate removal from solids, when noted, was carried out under vacuum drying overnight in an Abderhalden drying pistol over refluxing ethanol. All melting points were obtained using a Thomas-Hoover melting point apparatus and are corrected. $^1$H and $^{13}$C NMR were obtained using a Brucker AM-300 NMR spectrometer at 300 and 75.5 MHz, respectively. NMR solvents used were dueterochloroform ($CDCl_3$), methyl-$d_6$-sulfoxide (DMSO-$d_6$) and deuterium oxide ($D_2O$).

General Procedure for the Preparation of Esters of Examples 1–7

A mixture of the appropriate piperidine or piperazine (30 mmol), bromo ester (35 mmol), $K_2CO_3$ (40 mmol) and 80 mL of MeCN was refluxed overnight under N$_2$. After cooling to room temperature, the volatiles were removed in vacuo and the residue taken up in H$_2$O and extracted with CH$_2$Cl$_2$. The combined organic extracts were then washed with H$_2$O, brine, dried over MgSO$_4$, filtered and concentrated. The crude products were subjected to flash chromatography (SiO$_2$:MeOH:EtOAc, or CH$_2$Cl$_2$) to afford the purified products.

EXAMPLE 1

Preparation of 4-(3-Methoxyphenyl)-1-piperidineacetic acid, Methyl Ester, Maleic acid Salt The compound prepared by the above method was isolated after chromatography (74% yield) as a clear oil. The compound was isolated as a low melting waxy solid and characterized as the maleic acid salt: $^1$H NMR (DMSO-d$_6$) δ 7.24 (m, 1 H), 6.80 (m, 3 H), 6.08 (s, 2 H), 4.13 (s 2 H), 3.76 (s, 3 H), 3.74 (s, 3 H), 3.42 (m, 2 H), 3.04, (m, 2 H), 2.72 (p, 2 H, J=7.9 Hz), and 1.92 (m, 4 H); $^{13}$C NMR (DMSO-d$_6$) δ 167.2, 159.4, 146.0, 135.0, 129.6, 118.7, 112.5, 111.8, 55.5, 54.9, 52.0, 39.0, and 29.7. Analysis calculated for C$_{15}$H$_{21}$NO$_3$·C$_4$H$_4$O$_4$·0.25 H$_2$O: C, 59.45; H, 6.70; N, 3.65. Found: C, 59.45; H, 6.80; N, 3.47.

EXAMPLE 2

Preparation of 3-[4-(3-Methoxyphenyl)-]1-piperidinebutanoic acid, Methyl Ester, Maleic acid Salt The compound was isolated as a clear oil (86% yield) after chromatography and converted to the maleic acid salt. The salt was isolated as a colorless solid after recrystallization from Et$_2$O/MeCN: mp 103–4° C.; $^1$H NMR (DMSO-d$_6$) δ 7.24 (t, 1 H, J=7.8 Hz), 6.79 (m, 3 H), 6.03 (s, 2 H), 4.06 (q, 2 H, J=7.1 Hz), 3.72 (s, 3 H), 3.51 (m, 2 H), 3.36 (m, 2 H), 3.06 (m, 4 H), 2.79 (m, 1 H), 2.41 (t, 2 H, J=7.2 Hz), 1.88 (m, 6 H), and 1.79 (t, 3 H, J=7.1 Hz); $^{13}$C NMR (DMSO-d$_6$) δ 172.0, 167.3, 159.5, 145.8, 136.1, 129.7, 118.7, 112.6, 111.9, 60.2, 55.4, 55.0, 52.1, 38.7, 30.4, 19.2, and 14.1. Analysis calculated for C$_{18}$H$_{27}$NO$_3$·C$_4$H$_4$O$_4$: C, 62.69; H, 7.41; N, 3.32. Found: C, 62.59; H, 7.26; N, 3.09.

EXAMPLE 3

Preparation of 2-[4-(3-Methoxyphenyl )-]1-piperidinepropionic acid, Methyl Ester A solution of the piperidine (5.85 g, 30.6 mmol) and methyl acrylate (8.9 mL) was stirred at room temperature for 2.5 h. The volatiles were removed in vacuo and the residue then filtered through a plug of SiO$_2$ to furnish the acylsemicarbazide (7.83 g, 93% yield) as a very pale yellow oil: $^1$H NMR (CDCl$_3$) δ 7.19 (t, 1 H, J=7.8 Hz), 6.73 (m, 3 H), 3.76 (s, 3 H), 3.67 (s, 3 H), 3.01 (m, 2 H), 2.75 (m, 2 H), 2.53 (m, 2 H), 2.42 (m, 1 H), 2.09 (m, 2 H), and 1.76 (m, 4 H), $^{13}$C NMR (CDCl$_3$) δ 173.1, 159.7, 148.1, 129.4, 119.3, 112.7, 111.4, 55.2, 54.1, 54.0, 51.7, 42.7, 33.5, and 32.3. Anal. Calcd for C$_{16}$H$_{23}$NO$_3$: C, 69.29; H, 8.36; N, 5.05. Found: C, 69.08; H, 8.14; N, 5.04.

EXAMPLE 4

Preparation of 4-Phenyl-1-piperidineacetic acid, Methyl ester

The compound was prepared in a manner similar to that described in Example 1. After chromatography, the compound was isolated as a yellow oil (34% yield): $^1$H NMR (CDCl$_3$) δ 7.35 (m, 5 H), 3.75 (s, 3 H), 3.30 (s, 2 H), 3.08 (m, 2 H), 2.51 (m, 1 H), 2.30 (m, 2 H), 1.88 (m, 4 H).

EXAMPLE 5

Preparation of 4-Phenyl-1-piperazineacetic Acid, Methyl ester

The compound was prepared in a manner similar to that described in Example 1. The compound was isolated as a pale yellow oil (39% yield) after flash chromatography: $^1$H NMR (CDCl$_3$) δ 7.24 (m, 2 H), 6.88 (m, 3 H), 3.73 (s, 3 H), 3.26 (m, 6 H), 2.76 (t, 4 H, J=5.0 Hz), $^{13}$C NMR (CDCl$_3$) δ 170.7, 151.3, 129.2, 119.5, 116.3, 59.4, 53.1, 51.8, 49.1. Analysis calculated for C$_{13}$H$_{18}$N$_2$O$_2$: C, 66.64; H, 7.74; N, 11.96. Found: C, 66.36; H, 7.69; N, 11.82.

EXAMPLE 6

Preparation of 4-(1-Piperidinyl)-1-piperidineacetic acid, methyl ester

The reaction afforded an amber oil (53% yield) and was taken onto the next reaction without further characterization: $^1$H NMR (CDCl$_3$) δ 3.70 (m, 3 H), 3.19 (s, 2 H), 2.98 (d, 2 H, J=11.4 Hz), 2.54 (m, 4 H), 2.35 (m, 1 H), 2.15 (m, 2 H), 1.68 (m, 8 H), 1.43 (m, 2 H).

EXAMPLE 7

Preparation of 4-Cyclohexyl-1-piperazineacetic Acid, methyl ester

The compound was prepared according to standard literature procedure and obtained as a yellow oil (31% yield) after column chromatography and was used without further characterization.

General Procedure for the Preparation of Hydrazides of Examples 8–14

A solution of the acylsemicarbazide (23 mmol), NH$_2$NH$_2$·H$_2$O (69 mmol) and 65 mL of EtOH was refluxed overnight (20 h). The solvents were then removed in vacuo and the residues purified by flash chromatography (SiO$_2$:MeOH/CHCl$_3$ or CH$_2$Cl$_2$) to furnish the purified products as oils or low melting solids.

EXAMPLE 8

4-(3-Methoxyphenyl)-1-piperidineacetic acid hydrazide

The compound was isolated as a clear oil (92% yield) which slowly solidified on standing at room temperature to a colorless solid: mp 82–3° C.; $^1$H NMR (CDCl$_3$) δ 8.22 (br s, 1 H), 7.22 (m, 1 H), 6.74 (m, 3 H), 3.86 (br s, 2 H), 3.79 (s, 3 H), 3.09 (s, 2 H), 2.91 (m, 2 H), 2.46 (m, 1 H), 2.25 (m, 2 H), and 1.45 (m, 4 H); $^{13}$C NMR (CDCl$_3$) δ 170.9, 159.8, 147.6, 129.5, 119.2, 112.8, 111.4, 61.1, 55.2, 55.0, 42.0, and 33.6. Analysis calculated for C$_{14}$H$_{21}$N$_3$O$_2$: C, 63.85; H, 8.04; N, 15.96. Found: C, 63.70; H, 7.96; N, 15.69.

EXAMPLE 9

2-[4-(3-Methoxyphenyl)-1-piperidinepropionic acid hydrazide

The compound was isolated as a clear oil (57% yield): $^1$H NMR (DMSO-d$_6$) δ 9.00 (br s, 1 H)m 7.19 (t, 1 H, J=7.8

Hz), 6.75 (m 3 H), 4.14 (m, 2 H), 3.72 (s, 3 H), 2.92 (m, 2 H), 2.50 (t, 2 H, J=7.1 Hz), 2.45 (m, 1 H), 2.20 (t, 2 H, J=7.1 Hz), 1.97 (m, 2 H), and 1.66 (m, 4 H).

EXAMPLE 10

3-[4-(3-Methoxyphenyl)-1-piperidinebutanoic Acid hydrazide, hydrochloride salt

After chromatography, the compound was isolated as a clear oil (60% yield) and then a small portion converted to the HCl salt: mp indistinct; $^1$H NMR (DMSO-d$_6$) δ 11.26 (brs, 1 H), 11.05 (brs, 1 H), 10.56 (br s, 2 H), 7.25 (t, 1 H, J=8.3 Hz), 6.81 (m, 3 H), 3.73 (s, 3 H), 3.52 (m, 2 H), 3.04 (m, 4 H), 2.79 (m, 1 H), 2.38 (m, 2 H), and 2.00 (m, 6 H); $^{13}$C NMR (DMSO-d$_6$) δ 170.6, 159.4, 146.0, 129.7, 118.7, 112.7, 111.7, 55.1, 55.0, 51.9, 38.7, 29.9, 29.6, and 19.0. Analysis calculated for $C_{16}H_{25}N_3O_2 \cdot 2HCl \cdot 0.75\ H_2O$: C, 50.86; H, 7.60; N, 11.12. Found: C, 51.02; H, 7.77, N, 11.08.

EXAMPLE 11

4-Phenyl-1-piperidineacetic acid, hydrazide

This compound was isolated as an orange solid (71% yield): mp 88–90° C.; $^1$H NMR (CDCl$_3$) δ 8.21 (br s, 1 H), 7.27 (m, 6 H), 3.86 (br s, 1H), 3.10 (s, 2 H), 2.93 (d, 2 H, J=11.5 Hz), 2.50 (m, 1 H), 2.28 (m, 2 H), 1.77 (m, 4 H); $^{13}$C NMR (CDCl$_3$) δ 170.9, 145.8, 128.6, 126.8, 126.4, 61.2, 55.0, 41.9, 33.7, Analysis calculated for $C_{13}H_{19}N_3O$: C, 66.92; H, 8.21; N, 18.01. Found: C, 66.65; H, 8.48; N, 18.18.

EXAMPLE 12

4-Phenyl-1-piperazineacetic acid, hydrazide

After chromatography, the compound was obtained as a white solid (90% yield): mp 90–93° C.; $^1$H NMR (DMSO-d$_6$) δ 8.98 (br s, 1 H), 7.20 (t, 2 H, J=7.8 Hz), 6.91 (d, 2 H, J=8.4 Hz), 6.77 (t, 1 H, J=7.2 Hz), 4.28 (br s, 2 H), 3.13 (m, 4 H), 2.98 (s, 2 H), 2.59 (m, 4 H); $^{13}$C NMR (DMSO-d$_6$) δ 168.2, 151.0, 128.9, 118.8, 115.4, 59.9, 52.8, 48.1. Analysis calculated for $C_{12}H_{18}N_4O$: C, 61.52; H, 7.74; N, 23.91. Found: C, 61.49; H, 7.59; N, 23.96.

EXAMPLE 13

4-Cyclohexyl-1-piperazineacetic acid, hydrazide

This addition product of the hydrazide was furnished as a pale yellow solid (78% yield): mp indistinct; $^1$H NMR (DMSO-δ$_6$) δ 8.78 (s, 1 H), 4.15 (br s, 2 H), 3.35 (br s, 2 H), 2.85 (s, 2 H), 2.43 (m, 6 H), 2.15 (m, 1 H), 1.70 (m, 4 H), 1.55 (m, 1 H), 1.13 (m, 5 H).

EXAMPLE 14

4-(1-Piperidinyl)-1-piperidineacetic acid, hydrazide

The compound was obtained as a pale yellow residue (23% yield): $^1$H NMR (DMSO-δ$_6$) δ 8.84 (s, 1 H), 3.50 (br s, 2H), 2.94 (m, 2 H), 2.86 (s, 4 H), 2.16 (m, 1 H), 1.95 (m, 2 H), 1.63 (m, 2 H), 1.45 (m, 10 H), $^{13}$C NMR (DMSO-δ$_6$) δ 168.4, 61.6, 60.0, 53.1, 49.7, 27.3, 25.9, 24.4. HRMS Calcd. for $C_{12}H_{25}N_4O(M+H)$: 241.2028. Found: 241.2031.

General Procedure for the Preparation of Acyl- and Thioacylsemi-carbazides of Examples 15–24

To a solution of the starting hydrazide (22.8 mmol) in 65 mL of CH$_2$Cl$_2$, was added the corresponding isocyanate or thioisocyanate (23.0 mmol). The resulting solution was stirred overnight (15 h) at room temperature and then washed with H$_2$O, brine, and dried over Na$_2$SO$_4$. After filtration and concentration in vacuo, the residue was used crude or purified by flash chromatography (SiO$_2$:MeOH/CH$_2$Cl$_2$). The following Acyl- and Thioacylsemicarbazides were obtained.

EXAMPLE 15

4-[3-[[[2-[4-(3-Methoxyphenyl)-1-piperidinyl] acetyl]hydrazino]carbonyl]amino]phenyl-1,4-dihydro-2,6-dimethyl-3,5-pyridinedicarboxylic acid, dimethyl ester The compound was obtained as a clear foam (26% yield): mp indistinct; $^1$H NMR (DMSO-d$_6$) δ 9.51 (br s, 1 H), 8.88 (br s, 1 H), 8.66 (br s, 1 H), 7.88 (br s, 1 H), 7.21 (m, 3 H), 7.07 (t, 1 H, J=7.7 Hz), 6.76 (m, 4 H), 4.86 (s, 1 H), 3.73 (s, 3 H), 3.55 (s, 6 H), 3.34 (s, 2 H), 3.02 (m, 2 H), 2.45 (m, 1 H), 2.25 (s, 6 H), 2.19 (m, 2 H), and 1.71 (m, 4 H); $^{13}$C NMR (DMSO-d$_6$) δ 169.4, 167.4, 159.3, 155.2, 148.2, 148.0, 145.6, 139.9, 129.3, 128.3, 120.6, 118.9, 117.1, 116.1, 112.5, 111.3, 101.3, 60.3, 54.9, 53.8, 50.6, 38.4, 32.9, and 18.2. Analysis calculated for $C_{32}H_{39}N_5O_7 \cdot 0.81\ H_2O$: C, 61.96; H, 6.60; N, 11.29. Found: C, 61.96; H, 6.38, N, 11.23.

EXAMPLE 16

4-[3-[[[2-[3-[4-(3-Methoxyphenyl)-1-piperidinyl]-1-oxopropyl]hydrazino]carbonyl]amino]phenyl-1,4-dihydro-2,6-dimethyl-3,5-pyridinedicarboxylic acid, dimethyl ester This compound was obtained as a creamy white foam (29% yield): mp indistinct; $^1$H NMR (CDCl$_3$) δ 8.29 (br s, 1 H), 8.16 (br s, 1 H), 7.20 (m, 4 H), 7.07 (t, 1 H, J=7.7 Hz), 6.97 (d, 1 H, J=7.9 Hz), 6.74 (m, 4 H), 4.97 (s, 1 H), 3.78 (s, 3 H), 3.59 (s, 6 H), 3.01 (m, 2 H), 2.60 (m, 2 H), 2.43 (m, 3 H), 2.20 (s, 6 H), 2.03 (m, 2 H), and 1.78 (m, 4 H); $^{13}$C NMR (CDCl$_3$) δ 171.6, 168.4, 159.7, 155.3, 148.4, 147.6, 145.4, 138.6, 129.5, 128.5, 122.8, 119.4, 118.8, 117.8, 112.9, 111.4, 103.1, 55.2, 53.6, 51.0, 42.4, 39.0, 33.1, 31.0, and 19.1. Analysis calculated for $C_{33}H_{41}N_5O_7 \cdot 0.50\ H_2O$: C, 63.05; H, 6.73; N, 11.14. Found: C, 63.04; H, 6.66; N, 11.12.

EXAMPLE 17

4-[3-[[[2-[4-[4-(3-Methoxyphenyl)-1-piperidinyl]-1-oxobutyl]hydrazino]carbonyl]amino]phenyl-1,4-dihydro-2,6-dimethyl-3,5-pyridinedicarboxylic acid, dimethyl ester The compound was obtained as a pale pink solid (68% yield): mp 108–112° C. (sintered); $^1$H NMR (DMSO-d$_6$) δ 9.66 (br s, 1 H), 8.89 (br. s, 1 H), 8.66 (br s, 1 H), 8.26 (brs, 1 H), 7.19 (m, 3 H), 7.07 (t, 1 H, J=7.8 Hz), 6.77 (m, 4 H), 4.87 (s,. 1 H), 3.73 (s, 3 H), 3.56 (s, 6 H), 2.97 (m, 2 H), 2.50 (m, 1 H), 2.34 (m, 2 H), 2.26 (s, 6 H), 2.18 (t, 2 H, J=7.3 Hz), 1.98 (m, 2 H), and 1.67 (m, 6 H); $^{13}$C NMR (DMSO-d$_6$) δ 172.1, 167.4, 159.3, 155.3, 148.2, 148.0, 145.7, 139.4, 129.3, 128.3, 120.6, 118.9, 117.2, 116.2, 112.4, 111.4, 101.3, 57.5, 54.9, 53.7, 50.6, 42.0, 33.0, 31.2, 22.3, and 18.2. Analysis calculated for $C_{34}H_{43}N_5O_7 \cdot 0.24\ H_2O$: C, 64.01; H, 6.87; N, 10.98. Found: C, 64.01; H, 6.93; N, 10.79.

EXAMPLE 18

4-[3-[[[2-[(4-Phenyl-1-piperidinyl)acetyl]-hydrazino]-carbonyl]amino]phenyl]1,4-dihydro-2,6-dimethyl-3,5-pyridinedicarboxylic acid, dimethyl ester The compound was isolated as an off-white solid (99% yield): mp 138–143° C. (sintered); $^1$H NMR (DMSO-d$_6$) δ

8.88 (s, 1 H), 8.66 (s, 1 H), 7.88 (s, 1 H), 7.24 (m, 7 H), 7.07 (t, 1 H, J=7.7 Hz), 6.73 (d, 1 H, J=7.7 Hz), 4.87 (s, 1 H), 3.56 (s, 6 H), 3.35 (s, 2 H), 3.00 (m, 4 H), 2.46 (m, 2 H), 2.35 (m, 8 H), 1.77 (m, 4 H); $^{13}$C NMR (DMSO-d$_6$) δ 169.4, 167.4, 155.2, 148.2, 146.3, 145.7, 139.3, 128.3, 126.7, 120.6, 117.1, 116.1, 101.3, 60.2, 54.9, 50.6, 40.4, 38.4, 18.2. Analysis calculated for $C_{31}H_{37}N_5O_6$.1.0 $H_2O$: C, 62.72; H, 6.62; N, 11.80. Found: C, 62.68; H, 6.52; N, 11.68.

EXAMPLE 19

4-[3-[[[2-[(4-Phenyl-1-piperidinyl)acetyl]-hydrazino]-carbonothioyl]amino]phenyl]1,4-dihydro-2,6-dimethyl-3,5-pyridinedicarboxylic acid, dimethyl ester This compound was obtained as a light yellow solid (95% yield): mp 125–130° C. (sintered); $^1$H NMR (DMSO-d$_6$) δ 9.50 (br s, 1 H), 8.93 (s, 1 H), 7.21 (m, 8 H), 6.92 (d, 1 H, J=7.3 Hz), 4.90 (s, 1 H), 2.26 (s, 6 H), 2.19 (m, 2 H), 1.78 (m, 4 H); $^{13}$C NMR (DMSO-d$_6$) δ 180.3, 167.3, 148.7, 146.3, 145.9, 138.9, 128.3, 127.6, 126.7, 123.6, 101.3, 60.3, 54.9, 50.7, 41.3, 38.3, 32.9, 18.3. Analysis calculated for $C_{31}H_{37}N_5O_5S$.1.0 $H_2O$: C, 61.07; H, 6.45; N, 11.49. Found: C, 61.08; H, 6.51; N, 11.35.

EXAMPLE 20

4-[3-[[[2-[[4-(3-Methoxyphenyl)-1-piperidinyl)acetyl]-hydrazino]-carbonothioyl]amino]phenyl]1,4-dihydro-2,6-dimethyl-3,5-pyridinedicarboxylic acid, dimethyl ester The compound was isolated as a light yellow solid (quantitative): mp 113–116 ° C. (sintered); $^1$H NMR (DMSO-d$_6$) δ 9.51 (br s, 1 H), 8.92 (s, 1 H), 7.23 (m, 5 H), 6.91 (d, 1 H, J=7.3 Hz), 6.78 (m, 4 H), 4.88 (s, 1 H), 3.73 (s, 3 H), 3.55 (s, 6 H), 3.10 (s, 2 H), 2.98 (br s, 2 H), 2.26 (s, 6 H), 2.19 (m, 3 H), 1.75 (m, 4 H); $^{13}$C NMR (DMSO-d$_6$) δ 167.3, 159.3, 147.9, 145.9, 138.9, 129.3, 118.9, 112.5, 111.3, 101.2, 54.9, 53.9, 50.7, 38.3, 32.8, 18.2. Analysis calculated for $C_{32}H_{39}N_5O_6S$.0.85 $H_2O$: C, 60.33; H, 6.44; N, 10.99. Found: C, 60.68; H, 6.41; N, 10.56.

EXAMPLE 21

4-[3-[[[2-[(4-Phenyl)-1-piperazinyl]acetyl]-hydrazino]-carbonothioyl]amino]phenyl]1,4-dihydro-2,6-dimethyl-3,5-pyridinedicarboxylic acid, dimethyl ester This compound was isolated as a white solid (97%): mp 171–175° C. (sintered); $^1$H NMR (DMSO-d$_6$) δ 9.51 (br s, 1 H), 8.94 (s, 1 H), 7.25 (m, 5 H), 6.94 (d, 3 H, J=8.0 Hz), 6.77 (t, 1 H, J=7.2 Hz), 4.92 (s, 1 H), 3.56 (s, 6 H), 3.15 (m, 8 H), 2.66 (br s, 4 H), 2.28 (s, 6 H); $^{13}$C NMR (DMSO-d$_6$) δ 180.5, 167.4, 151.0, 147.8, 145.9, 138.9, 128.9, 127.6, 118.8, 115.3, 101.3, 59.9, 52.8, 50.7, 48.0, 38.3, 18.3. Analysis calculated for $C_{30}H_{36}N_6O_6S.H_2O$: C, 60.33; H, 6.16; N, 14.10. Found: C, 60.35; H, 6.23; N, 13.95.

EXAMPLE 22

4-[4-Fluoro-3-[[[2-[[4-(3-methoxyphenyl)-1-piperidinyl]acetyl]-hydrazino]-carbonothioyl]amino]phenyl]1,4-dihydro-2,6-dimethyl-3,5-pyridinedicarboxylic acid, dimethyl ester This compound was isolated as a white solid (98%): mp 114–120° C. (sintered); $^1$H NMR (DMSO-d$_6$) δ 8.96 (s, 1 H), 7.20 (t, 2 H, J=7.7 Hz), 7.04 (m, 2 H), 6.78 (m, 3 H), 4.86 (s, 1 H), 3.73 (s, 3 H), 3.55 (s, 6 H), 3.33 (br s, 2 H), 3.08 (s, 2 H), 2.96 (m, 2 H), 2.45 (m, 1 H), 2.26 (s, 6 H), 2.18 (m, 2 H); $^{13}$C NMR (DMSO-d$_6$) δ 167.2, 159.3, 148.0, 145.9, 143.4, 129.3, 126.4, 118.9, 114.8, 112.5, 111.3, 101.3, 60.2, 54.9, 53.9, 50.7, 41.4, 37.9, 32.8, 32.8, 18.2. Analysis calculated for $C_{32}H_{38}FN_5O_6S$.1.0 $H_2O$: C, 58.43; H, 6.13; N, 10.65. Found: C, 58.70; H, 6.10; N, 10.81.

EXAMPLE 23

4-[3-[[[2-[[4-(1-Piperidinyl)-1-piperidinyl]acetyl]-hydrazino]-carbonothioyl]amino]phenyl]1,4-dihydro-2,6-dimethyl-3,5-pyridinedicarboxylic acid, dimethyl ester This compound was obtained as a yellow solid (36%): mp indistinct; $^1$H NMR (DMSO-d$_6$) δ 7.24 (m, 3 H), 6.87 (d, 1 H, J=7.8 Hz), 4.88 (s, 1 H), 3.55 (s, 6 H), 3.44 (m, 4 H), 2.95 (m, 1 H), 2.73 (m, 1 H), 2.26 (s, 8 H), 2.08 (m, 1 H), 1.73 (m, 1 H), 1.38 (M, 4 H); $^{13}$C NMR (DMSO-d$_6$) δ 167.2, 149.8, 147.9, 146.3, 145.8, 139.3, 129.7, 127.8, 126.8, 123.9, 121.6, 101.1, 52.7, 50.7, 49.5, 38.3, 26.8, 18.3. HRMS calculated for $C_{30}H_{43}N_6O_5S$ (M+H): 599.3016. Found: 599.3034.

EXAMPLE 24

4-[3-[[[2-[(4-Cyclohexyl-1-piperazinyl) acetyl]-hydrazino]-carbonothioyl]amino]phenyl]1,4-dihydro-2,6-dimethyl-3,5-pyridinedicarboxylic acid, dimethyl ester This compound was isolated as a light yellow solid (73%): mp indistinct; $^1$H NMR (DMSO-d$_6$) δ 8.99 (m, 1 H), 7.31 (m, 3 H), 6.92 (m, 1 H), 4.95 (s, 1 H), 3.57 (m, 8 H), 3.09 (s, 1 H), 2.58 (m, 15 H), 1.82 (m, 5 H), 1.21 (m, 4 H); $^{13}$C NMR (DMSO-d$_6$) 167.4, 149.1, 147.7, 146.1, 145.9, 140.0, 128.6, 127.7, 115.9, 115.1, 101.3, 62.9, 59.5, 51.9, 51.0, 48.1, 38.3, 27.8, 27.5, 25.3, 18.2. HRMS calculated for $C_{30}H_{43}N_6O_5S$ (M+H): 599.3016. Found: 599.3030.

GENERAL PROCEDURE FOR THE PREPARATION OF OXADIAZOLES OF EXAMPLES 25–27

A solution of the acylsemicarbazide (3.5 mmol) and 19 mL of POCl$_3$ was heated on a steam bath until the reaction was judged complete by tlc analysis (45 minutes to 2 hours). The dark solution was cooled to room temperature, diluted with 100 mL of CH$_2$Cl$_2$ and the solution then poured into 300 mL of a stirred ice-water mixture. The mixture was allowed to warm to room temperature and then extracted with CH$_2$Cl$_2$/MeOH mixtures. The combined extracts were washed with H$_2$O, brine, and dried over MgSO$_4$. The volatiles were removed in vacuo and the residue purified by flash chromatography (SiO$_2$:EtOAc/MeOH). The following oxadiazole derivatives were obtained:

EXAMPLE 25

4-[3-[[5-[4-(Methoxyphenyl)-1-piperidinyl]methyl]-1,3,4-oxadiazol-2-yl]amino]phenyl]-1,4-dihydro-2,6-dimethyl-3,5-pyridinedicarboxylate, hydrochloride Salt This compound was isolated as an orange-yellow solid (8%): mp indistinct. Analysis calculated for $C_{33}H_{37}N_5O_6$.2 HCl.1.60 $H_2O$: C, 56.56; H, 6.06; N, 9.99. Found: C, 56.56; H, 6.06; N, 9.77.

EXAMPLE 26

4-[3-[[5-[4-(3-Methoxyphenyl)-1-piperidinyl]ethyl]-1,3,4-oxadiazol-2-yl]amino]phenyl]-1,4-dihydro-2,6-dimethyl-3,5-pyridinedicarboxylate, hydrochloride Salt This compound was isolated as a yellow solid (30% yield): mp 75-80° C. (sintered); $^{13}$C NMR (DMSO-$d_6$) δ 167.3, 160.0, 159.3, 156.3, 148.4, 145.8, 145.8, 145.7, 138.4, 129.5, 128.6, 120.3, 118.6, 115.9, 114.6, 112.6, 111.6, 101.1, 54.9, 52.6, 51.9, 51.8, 50.6, 38.2, 29.6, 20.0, and 18.1. HRMS calculated for $C_{33}H_{40}N_5O_6$ (M+H): 602.2979. Found: 602.2993.

EXAMPLE 27

4-[3-[[5-[3-[4-(3-Methoxyphenyl)-1-piperidinyl]propyl]-1,3,4-oxadiazol-2-yl]amino]phenyl]-1,4-dihydro-2,6-dimethyl-3,5-pyridinedicarboxylate, hydrochloride Salt This compound was isolated as a yellow solid (19% yield): mp indistinct; $^1$H NMR (DMSO-$d_6$) δ 10.85 (br s, 1 H), 10.35 (s, 1 H), 9.03 (s, 1 H), 7.37 (m, 2 H), 7.26 (t, 1 H, J=7.6 Hz), 7.16 (t, 1 H, J=1.8 Hz), 6.79 (m, 4 H), 4.91 (s, 1 H), 3.75 (s, 3 H), 3.66 (s, 6 H), 3.19 (m, 2 H), 3.05 (m, 2 H), 2.90 (t, 2 H, J=7.1 Hz), 2.80 (m, 1 H), 2.28 (s, 6 H), 2.19 (m, 4 H), and 1.92 (m, 2 H); $^{13}$C NMR (DMSO-$d_6$) δ 167.4, 159.9, 159.4, 158.7, 148.5, 146.0, 138.6, 129.7, 129.0, 120.3, 119.2, 118.7, 116.0, 114.6, 112.7, 111.7, 101.2, 55.0, 52.0, 50.7, 38.7, 38.4, 29.7, 22.1, 20.2, and 18.2. Analysis calculated for $C_{34}H_{41}N_5O_6 \cdot 1.5$ HCl$\cdot 0.33$ H$_2$O: C, 60.22; H, 6.43; N, 10.33. Found: C, 60.22; H, 6.42; N, 9.95.

GENERAL PROCEDURE FOR THE PREPARATION OF OXADIAZOLES OF EXAMPLES 28–32

The starting acyl- or thioacylsemicarbazide (0.34 mmol) was dissolved in 1,2-dichloroethane (10 mL). To this solution PPh$_3$ (0.41 mmol), and CCl$_4$ (0.51 mmol) was added and the solution was stirred at reflux for 36 hours. The solvent was concentrated in vacuo and the residue was purified by flash chromatography (SiO$_2$: MeOH/CH$_2$Cl$_2$). The following oxadiazole derivatives were obtained:

EXAMPLE 28

4-[3-[[5-[(4-Phenyl-1-piperidinyl)methyl]-1,3,4-oxadiazol-2-yl]amino]phenyl]-1,4-dihydro-2,6-dimethyl-3,5-pyridinedicarboxylate After flash chromatography, this compound was isolated as an off-white solid (54% yield): mp 118–123° C., sintered; $^1$H NMR (DMSO-$d_6$) δ 10.4 (s, 1 H), 8.92 (s, 1 H), 7.27 (m, 9 H), 6.76 (d, 1 H, J=7.6 Hz), 4.91 (s, 1 H), 3.71 (br s, 2 H), 3.57 (s, 6 H), 3.34 (s, 2 H), 2.95 (d, 2 H, J=10.3 Hz), 2.23 (m, 8 H), 1.68 (m, 4 H); $^{13}$H NMR (DMSO-$d_6$) δ 167.4, 160.2, 157.1, 148.4, 146.0, 145.9, 138.5, 128.7, 128.3, 126.7, 126.0, 120.3, 115.9, 114.5, 101.1, 53.2, 51.5, 50.7, 41.3, 38.3, 32.9, 18.2. HRMS calculated for $C_{31}H_{36}N_5O_5$ (M+H): 558.2717. Found: 558.2694.

EXAMPLE 29

4-[3-[[5-[(4-Phenyl-1-piperazinyl)methyl]-1,3,4-oxadiazol-2-yl]amino]phenyl]-1,4-dihydro-2,6-dimethyl-3,5-pyridinedicarboxylate This compound was isolated as a pale yellow airy solid (78% yield), after chromatography: mp 115–125° C., sintered; $^1$H NMR (DMSO-$d_6$) δ 10.4 (s, 1 H), 8.93 (s, 1 H), 7.38 (m, 2 H), 7.18 (m, 2 H), 6.92 (d, 2 H, J=8.1 Hz), 6.77 (m, 2 H), 4.92 (s, 1 H), 3.75 (s, 2 H), 3.57 (s, 6 H), 3.13 (m, 4 H), 2.63 (m, 4 H), 2.28 (s, 6 H); $^{13}$C NMR (DMSO-$d_6$) δ 167.4, 160.3, 156.8, 150.9, 148.5, 145.9, 138.5, 128.9, 128.7, 120.3, 118.9, 115.9, 115.5, 114.6, 101.1, 54.9, 52.2, 51.2, 50.7, 48.2, 38.3, 18.2. Analysis calculated for $C_{30}H_{34}N_6O_5 \cdot 0.25$ H$_2$O: C, 63.99; H, 6.18; N, 14.92. Found: C, 63.80; H, 6.18; N, 14.65.

EXAMPLE 30

4-[3-[[5-[(4-Cyclohexyl-1-piperazinyl) methyl]-1,3,4-oxadiazol-2-yl]amino]phenyl]-1,4-dihydro-2,6-dimethyl-3,5-pyridinedicarboxylate This compound was obtained as an orange solid (10% yield): mp 158–162° C., sintered; $^1$H NMR (DMSO-$d_6$) δ 10.4 (s, 1 H), 8.93 (s, 1 H), 7.30 (m, 3 H), 6.78 (m, 1 H), 4.91 (s, 1 H), 3.83 (s, 1 H), 3.74 (s, 1 H), 3.56 (s, 6 H), 3.16 (m, 8 H), 2.27 (s, 6 H), 1.44 (m, 11 H); $^{13}$C NMR (DMSO-$d_6$) δ 167.4, 156.0, 148.5, 145.8, 129.7, 128.7, 118.6, 112.5, 101.1, 54.9, 50.7, 48.8, 47.9, 43.6, 38.3, 29.4, 26.3, 24.4, 18.2. HRMS calculated for $C_{30}H_{41}N_6O_5$ (M+H): 565.3139. Found: 565.3150.

EXAMPLE 31

4-[4-Fluoro-3-[[5-[[4-(3-methoxyphenyl-1-piperidinyl)methyl]-1,3,4-oxadiazol-2-yl]amino]phenyl]-1,4-dihydro-2,6-dimethyl-3,5-pyridinedicarboxylate This compound was isolated as a pale yellow solid (34% yield): mp 199–203° C.; $^1$H NMR (DMSO-$d_6$) δ 10.1 (s, 1 H), 8.96 (s, 1 H), 7.98 (d, 1 J=6.4 Hz), 7.19 (t, 1 H, J=7.7 Hz), 7.08 (m, 1 H), 6.77 (m, 4 H), 4.92 (s, 1 H), 3.81 (m, 5 H), 3.58 (s, 6 H), 2.95 (d, 2 H, J=11.0 Hz), 2.45 (m, 1 H), 2.22 (m, 8 H), 1.68 (m, 4 H); $^{13}$C NMR (DMSO-$d_6$) δ 167.3, 160.4, 159.3, 157.7, 149.1, 147.7, 145.9, 144.0, 129.3, 125.9, 121.5, 119.4, 118.9, 114.9, 112.5, 111.4, 101.2, 54.9, 53.2, 51.6, 50.7, 41.4, 38.0, 32.8, 18.1. Analysis calculated for $C_{32}H_{36}FN_5O_6 \cdot 1.0$ H$_2$O: C, 61.63; H, 6.14; N, 11.23. Found: C, 61.78; H, 5.94; N, 11.04.

EXAMPLE 32

4-[3-[[5-[(4-Phenyl-1-piperidinyl)methyl]-1,3,4-oxadiazol-2-yl]amino]phenyl]-1,4-dihydro-2,6-dimethyl-3,5-pyridinedicarboxylate This compound was isolated as a yellow solid (28% yield): mp indistinct; $^1$H NMR (DMSO=$d_6$) δ 10.5 (s, 1 H), 8.94 (s, 1 H), 7.41 (m, 2 H), 7.18 (t, 1 H, J-7.9 Hz), 6.78 (d, 1 H, J=7.7 Hz), 4.91 (s, 1 H), 3.55 (s, 6 H), 3.38 (m, 6 H), 2.84 (m, 4 H), 2.27 (s, 6 H), 2.14 (m, 2 H), 1.77 (m, 6 H); $^{13}$C NMR (DMSO-$d_6$) δ 167.4, 160.7, 148.5, 145.9, 138.2, 130.3, 128.7, 120.6, 116.2, 114.8, 101.1, 50.7, 49.2, 38.3, 24.3, 22.7, 21.3, 18.2. LRMS m/z (ESI) 565.30 (M+H)$^+$; HPLC retention time 2.691.

EXAMPLE 33

Preparation of 4-[3-[[5-[(4-Phenyl-1-piperidinyl)methyl]-1,3,4-thiadiazol-2-yl]amino]phenyl]-1,4-dihydro-2,6-dimethyl-3,5-pyridinedicarboxylate A solution of the compound of Example 16 (0.25 g, 0.43 mmol) and Lawesson's reagent (0.35 g, 0.87 mmol) in toluene (50 mL) was refluxed for 2 hours. The mixture was cooled to room temperature, concentrated in vacuo, and filtered over a pad of silica gel. Final purification was achieved by preparatory HPLC. (10 mg, 4% yield) of compound was obtained after Prep HPLC: $^{13}$C NMR (CDCl$_3$) δ 168.1, 149.41, 146.9, 129.1, 127.6, 126.7, 114.0, 102.2, 55.3, 53.4, 51.1, 38.7, 30.4, 19.1. HRMS calculated for C$_{31}$H$_{36}$N$_5$O$_4$S (M+H): 574.2488. Found: 574.2489.

EXAMPLE 34

Preparation of (±)1,4-Dihydro-4-[3-[[4-(ethoxy)1,2,5-thiadiazole-3-yl-1-oxide]amino]phenyl]-2,6-dimethyl-3,5-pyridinedicarboxylic acid, Hemihydrate AlMe$_3$ (1.1 mL of a 2.0 M solution in hexanes; 2.2 mmol) was added to a solution of requisite aniline (316 mg, 1.0 mmol) in CH$_2$Cl$_2$ (10 mL) at 0° C. The mixture was stirred for 30 minutes at 0° C., followed by the addition of the thiadiazole (285 mg, 1.5 mmol). The reaction was then brought to reflux for 18 hours, cooled to 0° C., and quenched by slow addition of salt. NH$_4$Cl. The crude product was extracted with CH$_2$Cl$_2$, dried, and concentrated. The residue was chromatographed (CH$_2$Cl$_2$:MeOH 50:1) to afford the desired product (220 mg, 48%). mp 191–197° C. $^1$H NMR (DMSO-d$_6$): δ 10.30 (s, 1 H), 8.94 (s, 1 H), 7.84 (s, 1 H), 7.64 (d, 1 H, J=8.0 Hz), 7.24 (t, 1 H, J=8.0 Hz), 6.94 (d, 1 H, J=8.0 Hz), 4.93 (s, 1 H), 4.55 (m, 2 H), 3.56 (s, 6 H), 2.27 (s, 6 H), 1.45 (t, 3 H, J=7.1 Hz). $^{13}$C NMR (DMSO-d$_6$): δ 167.3, 164.0, 152.6, 148.3, 145.9, 137.7, 128.4, 123.4, 119.5, 118.3, 101.0, 68.9, 50.7, 38.4, 18.2, 13.8. Analysis calculated for C$_{21}$H$_{24}$N$_4$O$_6$S.0.5 H$_2$O: C, 53.72; H, 5.37; N, 11.93. Found: C, 53.94; H, 5.25; N, 12.17.

EXAMPLE 35

Preparation of (±)4-[3-[[3-[[4-(3-Methoxyphenyl)-1-piperidinyl]propyl]amino]1,2,5-thiadiazol-2-yl-1-oxide]amino]phenyl]-1,4-dihydro-2,6-dimethyl-3,5-pyridinedicarboxylic acid, dimethyl ester, Dihydrate The thiadiazole of Example 34 (263 mg, 0.30 mmol) and the piperdine of Compound XII (149 mg, 0.60 mmol) were combined in CH$_3$CN (3.0 mL) and stirred for 18 hours. The resulting solution was concentrated and chromatographed (CH$_2$Cl$_2$:MeOH, 10:1) to give the thiadiazole oxide (110 mg, 55%). mp 128–134° C. $^1$H NMR (CDCl$_3$): δ 7.45 (bs, 1 H), 7.11 (t, 1 H, J=7.8 Hz), 7.00 (d, 1 H, J=7.8 Hz), 6.68 (m, 6 H), 6.36 (bs, 1 H), 4.97 (s, 1 H), 3.70 (s, 3 H), 3.54 (s, 6 H), 3.29 (m, 1 H), 3.19 (m, 1 H), 2.98 (m, 2 H), 2.42 (m, 3 H), 2.26 (s, 3 H), 2.19 (s, 3 H), 2.08 (m, 2 H), 1.75 (m, 6 H). $^{13}$C NMR (CDCl$_3$): δ 168.1, 159.7, 159.2, 153.5, 148.2, 147.4, 145.5, 145.4, 137.7, 129.5, 128.7, 124.4, 119.9, 119.2, 118.1, 112.9, 111.4, 103.1, 102.9, 55.8, 55.2, 54.2, 54.1, 51.2, 51.1, 42.6, 42.2, 38.8, 32.9, 25.1, 19.7, 19.5. Analysis calculated for C$_{34}$H$_{42}$N$_6$O$_6$S.1.9 H$_2$O: C, 58.58; H, 6.62; N, 12.05; Found: C, 58.97; H, 6.32; N, 11.65. HRMS calculated for C$_{34}$H$_{43}$N$_6$O$_6$S: 663.2965. Found: 663.2976.

While various embodiments are disclosed herein, these compounds are intended to be exemplary of the invention. It will be appreciated by one skilled in the art that other compounds can be prepared without departing from the scope of the invention as defined in the appended claims.

What is claimed is:

1. A compound of Formula (I) or its pharmaceutically acceptable acid addition salts or hydrates thereof

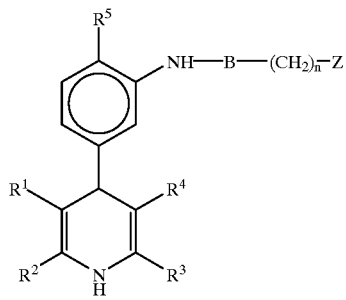

(I)

wherein B is

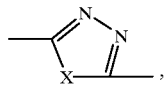

or

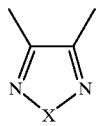

with X being O, S or

and $X^1$ is O or S;
$R^1$ and $R^4$ are independently selected from the group consisting of $CO_2R^6$, cyano, and

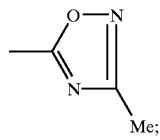

$R^2$ and $R^3$ are independently selected from the group consisting of hydrogen, cyano and lower alkyl;
$R^5$ is selected from either hydrogen or halogen;
$R^6$ is lower alkyl;
n is an integer selected from 1 to 5;

Z is 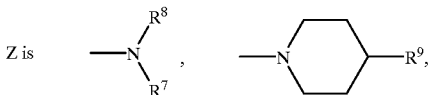

or

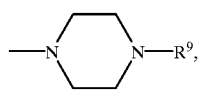

in which $R^7$ and $R^8$ are independently selected from the group consisting of lower alkyl and hydroxy-lower-alkyl; $R^9$ is selected from the group consisting of hydrogen, lower alkyl, $-CO_2R^6$, $-(CH_2)_mR^{10}$, hydroxy, cyano, and $-(CH_2)_mNR^{11}R^{12}$, wherein m is zero or an integer from 1 to 3;

$R^{10}$ is $C_{3-7}$ cycloalkyl, naphthyl, or

with $R^{13}$ selected from the group consisting of lower alkyl, lower alkenyl, $C_{3-7}$ cycloalkyl, lower alkoxy, hydrogen, halogen, hydroxy, dialkylamino, phenoxy, amino, —NHCOR$^6$, —CO$_2$R$^6$, NO$_2$, trifluoromethyl, and phenyl, and $R^{11}$ and $R^{12}$ are independently selected from the group consisting of hydrogen, alkyl, cycloalkyl, phenyl, alkylamino, heterocyclic alkyl, methoxy, cyano, hydroxy-lower alkyl, naphthyl, furfuryl, tetrahydrofurfuryl, thienyl, azetidinyl, —CO$_2$R$^6$, —CH$_2$CONH$_2$, and —O$_2$CNH$_2$ and where —NR$^{11}$R$^{12}$ is a heterocyclic amine or imine.

2. A compound of claim 1, wherein B is

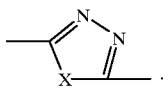

3. A compound of claim 2 wherein Z is

4. A compound of claim 2 wherein Z is

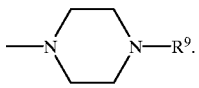

5. A compound of claim 3 wherein $R^9$ is

6. A compound of claim 1, wherein $R^1$ and $R^4$ are —CO$_2$CH$_3$.

7. The compound of claim 1 wherein n is 1, 2 or 3.

8. The compound of claim 1 wherein Z is

and $R^9$ is 3-methoxyphenyl, phenyl or cyclohexyl.

9. The compound of claim 1 wherein B is

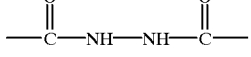

and Z is

10. The compound of claim 9 wherein $R^9$ is 3-methyoxyphenyl or phenyl.

11. The compound of claim 2 wherein Z is 3-methoxyphenylpiperidinyl.

12. The compound of claim 1 selected from the group consisting of

4-[3-[[[2-[4-(3-Methoxyphenyl)-1-piperidinyl]acetyl] hydrazino]carbonyl]amino]phenyl-1,4-dihydro-2,6-dimethyl-3,5-pyridinedicarboxylic acid, dimethyl ester;

4-[3-[[[3-[4-(3-Methoxyphenyl)-1-piperidinyl]-1-oxopropyl]hydrazino]carbonyl]amino]phenyl-1,4-dihydro-2,6-dimethyl-3,5-pyridinedicarboxylic acid, dimethyl ester;

4-[3-[[[4-[4-(3-Methoxyphenyl)-1-piperidinyl]-1-oxobutyl]hydrazino]carbonyl]amino]phenyl-1,4-dihydro-2,6-dimethyl-3,5-pyridinedicarboxylic acid, dimethyl ester;

4-[3-[[[2-[(4-Phenyl-1-piperidinyl)acetyl]-hydrazino]-carbonyl]amino]phenyl]1,4-dihydro-2,6-dimethyl-3,5-pyridinedicarboxylic acid, dimethyl ester;

4-[3-[[[2-[(4-Phenyl-1-piperidinyl)acetyl]-hydrazino]-carbonothioyl]amino]phenyl]1,4-dihydro-2,6-dimethyl-3,5-pyridinedicarboxylic acid, dimethyl ester;

4-[3-[[[2-[(4-(3-Methoxyphenyl)-1-piperidinyl)acetyl]-hydrazino]-carbonothioyl]amino]phenyl]1,4-dihydro-2,6-dimethyl-3,5-pyridinedicarboxylic acid, dimethyl ester;

4-[3-[[[2-[(4-Phenyl)-1-piperazinylacetyl]-hydrazino]-carbonothioyl]amino]phenyl]1,4-dihydro-2,6-dimethyl-3,5-pyridinedicarboxylic acid, dimethyl ester;

4-[4-Fluoro-3-[[[2-[[4-(3-methoxyphenyl)-1-piperidinyl] acetyl]-hydrazino]-carbonothioyl]amino]phenyl]1,4-dihydro-2,6-dimethyl-3,5-pyridinedicarboxylic acid, dimethyl ester;

4-[3-[[[2-[[4-(1-Piperidinyl)-1-piperidinyl]acetyl]-hydrazino]-carbonothioyl]amino]phenyl]1,4-dihydro-2,6-dimethyl-3,5-pyridinedicarboxylic acid, dimethyl ester; and 4-[3-[[[2-[(4-Cyclohexyl-1-piperazinyl) acetyl]-hydrazino]-carbonothioyl]amino]phenyl]1,4-dihydro-2,6-dimethyl-3,5-pyridinedicarboxylic acid, dimethyl ester.

13. The compound of claim 1 selected from the group consisting of

4-[3-[[5-[[4-(3-Methoxyphenyl)-1-piperidinyl]methyl]-1,3,4-oxadiazol-2-yl]amino]phenyl]-1,4-dihydro-2,6-dimethyl-3,5-pyridinedicarboxylate, hydrochloride salt;

4-[3-[[5-[2-[4-(3-Methoxyphenyl)-1-piperidinyl]ethyl]-1,3,4-oxadiazol-2-yl]amino]phenyl]-1,4-dihydro-2,6-dimethyl-3,5-pyridinedicarboxylate, hydrochloride salt; and 4-[3-[[5-[3-[4-(3-Methoxyphenyl)-1-piperidinyl]propyl]-1,3,4-oxadiazol-2-yl]amino]phenyl]-1,4-dihydro-2,6-dimethyl-3,5-pyridinedicarboxylate, hydrochloride salt.

14. The compound of claim 1 selected from the group consisting of

4-[3-[[5-[(4-Phenyl-1-piperidinyl)methyl]-1,3,4-oxadiazol-2-yl]amino]phenyl]-1,4-dihydro-2,6-dimethyl-3,5-pyridinedicarboxylate;

4-[3-[[5-[(4-Phenyl-1-piperazinyl)methyl]-1,3,4-oxadiazol-2-yl]amino]phenyl]-1,4-dihydro-2,6-dimethyl-3,5-pyridinedicarboxylate;

4-[3-[[5-[(4-Cyclohexyl-1-piperazinyl)methyl]-1,3,4-oxadiazol-2-yl]amino]phenyl]-1,4-dihydro-2,6-dimethyl-3,5-pyridinedicarboxylate;

4-[4-fluoro-3-[(5-[[4-(3-Methoxyphenyl-1-piperidinyl)methyl]-1,3,4-oxadiazol-2-yl]amino]phenyl]-1,4-dihydro-2,6-dimethyl-3,5-pyridinedicarboxylate; and 4-[3-[[5-[(4-Piperdine-1-piperidinyl)methyl]-1,3,4-oxadiazol-2-yl]amino]phenyl]-1,4-dihydro-2,6-dimethyl-3,5-pyridinedicarboxylate.

15. The compound of claim 1 selected from the group consisting of

4-[3-[[5-[(4-Phenyl-1-piperidinyl)methyl]-1,3,4-thiadiazol-2-yl]amino]phenyl]-1,4-dihydro-2,6-dimethyl-3,5-pyridinedicarboxylate; and (±)4-[3-[[3-[[4-(3-Methoxyphenyl)-1-piperidinyl]propyl]amino]1,2,5-thiadiazol-2-yl-1-oxide]amino]phenyl]-1,4-dihydro-2,6-dimethyl-3,5-pyridinedicarboxylic acid, dimethyl ester, dihydrate.

16. A method of promoting weight loss and treating eating disorders in a mammal comprising administering to a mammalian host an effective dose of a compound claimed in claim 1.

17. A pharmaceutical composition for use in promoting weight loss and treating eating disorders, the composition comprising an effective amount of a compound claimed in claim 1 in combination with a pharmaceutically acceptable carrier.

* * * * *